(12) United States Patent
Gao et al.

(10) Patent No.: US 12,312,300 B2
(45) Date of Patent: *May 27, 2025

(54) PROCESS FOR RECOVERING CLOSE BOILING PRODUCTS

(71) Applicant: LanzaTech, Inc., Skokie, IL (US)

(72) Inventors: Allan Haiming Gao, Skokie, IL (US); Robert John Conrado, Skokie, IL (US); Derek Wayne Griffin, Skokie, IL (US); Peng Tian, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/386,206

(22) Filed: Nov. 1, 2023

(65) Prior Publication Data

US 2024/0059628 A1 Feb. 22, 2024

Related U.S. Application Data

(60) Continuation of application No. 17/443,929, filed on Jul. 28, 2021, now Pat. No. 11,807,592, which is a
(Continued)

(51) Int. Cl.
*C07C 29/84* (2006.01)
*B01D 3/10* (2006.01)
(Continued)

(52) U.S. Cl.
CPC .............. *C07C 29/84* (2013.01); *B01D 3/10* (2013.01); *B01D 3/40* (2013.01); *B01J 2/12* (2013.01);
(Continued)

(58) Field of Classification Search
CPC ........... C07C 29/84; C07C 31/04; B01D 3/10; B01D 3/34; B01D 3/40; B01D 53/26; B01D 61/36; B01D 36/02
See application file for complete search history.

(56) References Cited

U.S. PATENT DOCUMENTS 5,800,681 A * 9/1998 Berg ...................... C07C 29/84
203/64
5,897,750 A * 4/1999 Berg ...................... C07C 45/83
203/64

(Continued)

FOREIGN PATENT DOCUMENTS

CN 113387773 A 9/2021

OTHER PUBLICATIONS

Kumar et al., "Anhydrous Ethanol: A Renewable Sourse of Energy", Renewable & Sustainable Energy Reviews, 14, 2010, p. 1830-1844.

*Primary Examiner* — Yate' K Cutliff

(57) ABSTRACT

The disclosure is directed to a method for recovering products from a fermentation broth. The disclosure relates to the use of extractive distillation to recover products which have close boiling points, such as ethanol and isopropanol, from a fermentation broth. In an embodiment, the recovery of product is completed in a manner that minimizes stress on the microbial biomass, such that it remains viable, at least in part, and may be recycled and reused in the fermentation process, which may result in increased efficiency in the fermentation process. The extractive distillation vessel reactor may be used downstream of a distillation vessel. To minimize stress on the microbial biomass the distillation vessel may be under vacuum. The extractive distillation vessel may be used alongside a separation vessel such that the separation vessel is capable of recycling extractive distillation agent.

25 Claims, 3 Drawing Sheets

Related U.S. Application Data division of application No. 16/723,354, filed on Dec. 20, 2019, now Pat. No. 11,091,415.

(60) Provisional application No. 62/803,120, filed on Feb. 8, 2019.

(51) Int. Cl.
| | |
|---|---|
| *B01D 3/40* | (2006.01) |
| *B01J 2/12* | (2006.01) |
| *B01J 21/04* | (2006.01) |
| *B01J 21/12* | (2006.01) |
| *C07C 1/24* | (2006.01) |
| *C07C 11/04* | (2006.01) |
| *C07C 11/06* | (2006.01) |
| *C07C 45/81* | (2006.01) |
| *B01D 3/34* | (2006.01) |

(52) U.S. Cl.
CPC ............... *B01J 21/04* (2013.01); *B01J 21/12* (2013.01); *C07C 1/24* (2013.01); *C07C 11/04* (2013.01); *C07C 11/06* (2013.01); *C07C 45/81* (2013.01); *B01D 3/34* (2013.01)

(56) References Cited

U.S. PATENT DOCUMENTS

| | | |
|---|---|---|
| 6,368,819 B1 | 4/2002 | Gaddy |
| 6,755,975 B2 * | 6/2004 | Vane ................. B01D 61/3621 95/41 |
| 2006/0194999 A1 | 8/2006 | Brown |
| 2010/0294642 A1 | 11/2010 | Datta |
| 2015/0224420 A1 | 8/2015 | Hickey |
| 2017/0022124 A1 | 1/2017 | Aribert |
| 2018/0264375 A1 * | 9/2018 | Sechrist ............. B01D 19/0057 |
| 2021/0284925 A1 | 9/2021 | Gao et al. |

* cited by examiner

PROCESS FOR RECOVERING CLOSE BOILING PRODUCTS

CROSS REFERENCE TO RELATED APPLICATIONS

This application is a continuation of U.S. patent application Ser. No. 17/443,929 filed on Jul. 28, 2021 which is a division of U.S. patent application Ser. No. 16/723,354 filed Dec. 20, 2019, now U.S. Pat. No. 11,091,415 B2, issued on Aug. 7, 2021, which claims the benefit of U.S. Provisional Patent Application No. 62/803,120 filed Feb. 8, 2019, the entirety of which are incorporated herein by reference.

FIELD OF THE DISCLOSURE

This disclosure relates to a method for recovering products with close boiling points from a fermentation broth. In particular, the disclosure relates to the use of extractive distillation to recover products, such as ethanol and isopropanol, from a fermentation broth, where the fermentation broth contains microbial biomass, ethanol, and isopropanol.

BACKGROUND

Carbon dioxide ($CO_2$) accounts for about 76% of global greenhouse gas emissions from human activities, with methane (16%), nitrous oxide (6%), and fluorinated gases (2%) accounting for the balance (the United States Environmental Protection Agency). The majority of $CO_2$ comes from the burning of fossil fuels to produce energy, although industrial and forestry practices also emit $CO_2$ into the atmosphere. Reduction of greenhouse gas emissions, particularly $CO_2$, is critical to halting the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and isopropanol.

Typically, products produced through either Fischer-Tropsch and/or gas fermentation are separated through conventional distillation. The distillation process is based on the difference in the volatility, i.e., the difference in boiling point, of the components to be separated. However, for close boiling mixtures, such as mixtures containing both ethanol and isopropanol, conventional distillation has been shown to be unable to effectively separate individual components from the solution.

Further, C1-fixing microorganisms present in the fermentation broth are unlikely to survive the high temperatures required for conventional distillation. To overcome the loss of viable C1-fixing microorganisms, filtration methods have been employed. However, over time, with traditional filtration methods, particulate matter can build up in or on the filter, which can lead to a reduction in the filtrate flux, ultimately requiring cleaning and/or replacement of the filter.

Accordingly, there remains a need for a system that is effective at separating compounds with similar boiling points, such as ethanol and isopropanol, while ensuring the viability of the C1-fixing microorganisms in the fermentation broth.

BRIEF SUMMARY

The disclosure provides a method for recovering product from a fermentation broth, comprising microbial biomass, ethanol, and isopropanol. In an embodiment, the fermentation broth is passed from a bioreactor to a vacuum distillation vessel where the fermentation broth is partially vaporized to produce a product enriched stream comprising ethanol and isopropanol, and a product depleted stream comprising microbial biomass. In some embodiments, at least a portion of the product depleted stream is passed back to the bioreactor. In a next step, an extractive distillation vessel may be used to separate the ethanol and isopropanol. Separation is achieved through distillation in the presence of an extractive distillation agent to obtain an overhead product and distillation bottoms. Depending on the extractive distillation agent used, either ethanol or isopropanol are recovered in the overhead product with at least a portion of the other product, ethanol if isopropanol is recovered in the overhead product and isopropanol if ethanol is recovered in the overhead product, being recovered in the distillation bottoms.

The extractive distillation agent works by interacting with a product, either ethanol or isopropanol, within the product enriched stream to increase the relative volatility between the products. In an embodiment, the extractive distillation agent has a high affinity for one product, either ethanol or isopropanol, and a low affinity for the alternative product. A proper extractive distillation agent should not form an azeotrope with components in the product enriched stream and should be capable of being separated from the alternative product by a subsequent separation vessel, typically through distillation.

To recover ethanol in the overhead product and isopropanol in the distillation bottoms, the extractive distillation agent may comprise at least one material selected from the group consisting of alpha-pinene, beta-pinene, methyl isobutyl ketone, limonene, alpha-phellandrene, alpha-terpinene, myrcene, carane, p-mentha-1,5-diene, butyl ether, 1-methoxy-2-propanol, n-butyl acetate, n-amyl acetate, benzyl acetate, ethylene glycol ethyl ether acetate, methyl acetoacetate, ethylene glycol diacetate, 2-butoxyethyl acetate, methyl butyrate, ethyl propionate, ethyl n-valerate, butyl benzoate, ethyl benzoate, pyridine, N,N-dimethyl aniline, o-sec.butyl phenol, 3-isopropyl phenol, 2,6-dimethyl phenol, o-tert.butyl phenol, 4-ethyl phenol, diethyl phthalate, diisooctyl phthalate, dimethyl adipate, glycerine triacetate, diethyl malonate, dimethyl glutarate, tetrahydrofuran, ethylene glycol phenyl ether, dipropylene glycol methyl ether acetate, diethylene glycol hexyl ether, propoxypropanol, butoxypropanol, p-xylene glycol dimethyl ether, diethylene glycol t-butyl ether methyl ether, triethylene glycol diacetate, anisole, phenetole, phenyl ether, 1,2-methylenedioxybenzene, isophorone, ethyl-3-ethoxypropionate, tetraethylorthosilicate, 2-hydroxyacetophenone, 1,1,1-trichloroethane, tetrachloroethylene, 2,2,2-trichloroethanol, m-dichlorebenzene, chlorobenzene, 2,6-dichlorotoluene, 1-chlorohexane, diethylene glycol, dimethyl sulfoxide, dimethylformamide, sulfolane, isophorone, 2-pyrrolidione, 1-methyl-2pyrrolindinone, isodecyl alcohol, cyclododecanol, benzyl alcohol, 1-dodecanol, tridecyl alcohol, phenethyl alcohol, cyclohexanol, cyclopentanol, 2-nitropropane, 1-nitropropane, nitro-ethane, nitromethane, 3-nitrotoluene, 2-nitrotoluene, triacetin, 3-nitro-o-xylene, 1,4-dioxane, isobutyl acetate, ethyl butyrate, isoamyl formate, methyl caproate, ethyl caproate, propyl caproate, 1-methoxy-2-propanol acetate, isobutyl isobutyrate, hexyl acetate, ethyl isobutyrate, propyl butyrate, isobutyl butyrate, isobornyl acetate, 1,3-dioxolane, nitrobenzene, butyl butyrate, 4-methyl-2-pentanone, and polyethylene glycol 400.

In an embodiment, the extractive distillation agent is added to the extractive distillation vessel at least at a 5:1 extractive distillation agent to isopropanol ratio. In at least one embodiment, the extractive distillation agent is added at least at a 5:1, 10:1, 20:1, or 40:1 extractive distillation agent to isopropanol ratio.

To recover isopropanol in the overhead product and ethanol in the distillation bottoms, the extractive distillation agent may comprise at least one material selected from the group consisting of ethyl benzene, toluene, p-xylene, heptane, phenol, and 2-tert-butyl phenol.

In an embodiment, the extractive distillation agent is added to the extractive distillation vessel at least at a 5:1 extractive distillation agent to ethanol ratio. In at least one embodiment, the extractive distillation agent is added at least at a 5:1, 10:1, 20:1, or 40:1 extractive distillation agent to ethanol ratio.

In certain instances, the fermentation broth may further comprise one or more by-product selected from the group consisting of acetic acid, acetone, 3-hydroxybutyrate, isobutanol, n-propanol, n-butanol, and/or 2,3-butanediol. At least a portion of at least one by-product is removed through a side draw or subsequent process. In an embodiment, at least a portion of 3-hydroxybutyrate, isobutanol, n-propanol, and/or n-butanol are removed through a side draw in the rectification column.

In certain instances, the acetone in the fermentation broth is used as an intermediate to produce isopropanol. When acetone is used as an intermediate for producing isopropanol, at least a portion of the acetone in the fermentation broth is converted to isopropanol by one or more microorganism within the bioreactor. In various embodiments, at least a portion of the acetone is removed from the fermentation broth prior to the fermentation broth being passed to the vacuum distillation vessel. In various embodiments, at least a portion of the acetone is separated using a heat exchanger, located downstream of a rectification column. In an embodiment, at least a portion of the removed acetone is recycled to the bioreactor to increase the proportion of isopropanol produced by the fermentation process.

In certain instances, the process is optimized to produce isopropanol over ethanol. To increase the proportion of isopropanol produced by the fermentation process, at least a portion of the separated ethanol that is produced in the bioreactor may be passed back to the bioreactor to decrease the proportion of ethanol subsequently produced in the bioreactor. In an embodiment, the passing of ethanol back to the bioreactor will decrease the amount of carbon that is fixed to produce ethanol and will increase the amount of carbon that is fixed to produce isopropanol. In certain instances where acetone is an intermediate for producing isopropanol, the passing of ethanol back to the bioreactor decreases the proportion of carbon that is fixed to produce ethanol and increases the amount of carbon that is fixed to produce acetone. At least a portion of the ethanol passed back to the bioreactor may be passed from either the extractive distillation vessel, or the separation vessel, depending on what extractive distillation agent is utilized, and where ethanol is recovered in the process.

The disclosure provides for the optimization of energy consumed by the process. In an embodiment, the extractive distillation vessel is heat integrated to reduce the amount of energy required by the process. In certain instances, the disclosure provides for the contacting of the overhead product produced in the extractive distillation column with the reboiler of the separation vessel, reboiler of the rectification column, and/or the heat exchanger to reduce the amount of energy required by the process. Prior to being used as a heat exchange medium, one or more overhead product may be compressed to increase the pressure of the stream. The overheads produced in other vessels/columns may be used as a heat exchange medium as well. For example, the overhead product produced by the rectification column may contact the reboiler of the extractive distillation vessel, reboiler of the separation vessel, and/or the heat exchanger to reduce the amount of energy required by the process.

The disclosure provides for the maximization of producing certain products, while also minimizing the production of by-products. In an embodiment, a separation vessel is used to separate the product contained in the distillation bottoms from the extractive distillation agent. In one embodiment, the separation vessel can receive the distillation bottoms and produce an isopropanol enriched stream and an extractive distillation agent enriched stream. In another embodiment, the separation vessel can receive the distillation bottoms and produce an ethanol enriched stream and an extractive distillation agent enriched stream. Whether or not the separation vessel produces an isopropanol enriched stream or an ethanol enriched stream is dependent at least in part on the extractive distillation agent utilized. In an embodiment, at least a portion of the extractive distillation agent enriched stream is passed to the extractive distillation vessel to reduce the amount of new extractive distillation agent required by the extractive distillation vessel.

In an embodiment the disclosure is capable of processing fermentation broth at a given feed rate. The feed rate is defined in terms of bioreactor volumes of fermentation broth per hour. In at least one embodiment, the feed rate to the vacuum distillation vessel is between 0.05 to 0.5 bioreactor volumes per hour. In certain embodiments, the feed rate is between 0.01 to 0.1, 0.05 to 0.2, 0.05 to 0.3, 0.05 to 0.4, 0.1 to 0.3, 0.1 to 0.5, or 0.3 to 0.5 bioreactor volumes per hour.

In certain instances, the fermentation broth has a given residence time in the vacuum distillation vessel. The amount of time the fermentation broth is within the vacuum distillation vessel is the amount of time between the moment the fermentation broth enters through the inlet for receiving the fermentation broth, and when the fermentation broth exits through the outlet for transferring the product depleted stream. In an embodiment, the residence time is between 0.5 and 15 minutes. In various embodiments, the residence time is between 0.5 and 12 minutes, 0.5 and 9 minutes, 0.5 and 6 minutes, 0.5 and 3 minutes, 2 and 15 minutes, 2 and 12 minutes, 2 and 9 minutes, or 2 and 6 minutes. In at least one embodiment, the residence time is less than 15 minutes, less than 12 minutes, less than 9 minutes, less than 6 minutes, less than 3 minutes, less than 2 minutes, or less than 1 minute to ensure the viability of the microorganisms.

In certain instances, the vacuum distillation vessel defines a separation section comprised of a series of distillation trays. The distillation trays may be any suitable series of distillation trays to provide adequate vapor-liquid contact.

In certain instances, the vacuum distillation vessel defines a separation section comprised of packing material. The packing material may be any suitable material capable of providing adequate vapor-liquid contact.

The separation section of the vacuum distillation vessel is designed to provide a plurality of theoretical distillation stages whereby an increasing amount of product is vaporized from the fermentation broth as the fermentation broth passes through the distillation stages. In an embodiment, the separation medium provides multiple theoretical distillation stages. In certain embodiments, the separation medium provides at least three theoretical distillation stages, or at least five theoretical distillation stages, or at least six theoretical distillation stages.

In an embodiment the separation is carried out so as to ensure the viability of the microbial biomass. By ensuring the viability of the microbial biomass, the product depleted stream being passed to the bioreactor, which contains at least some viable microorganisms, may again be utilized for the gas fermentation process. The product depleted stream comprises microbial biomass that is at least 20% viable, at least 25% viable, at least 30% viable, at least 40% viable, at least 50% viable, or at least 60% viable, or at least 70% viable, or at least 80% viable, or at least 85% viable, or at least 90% viable, or at least 95% viable. As used herein percent viable describes the viable cell count divided by the total cell count where the total cell count is a sum of the viable cell count and the non-viable cell count. In an embodiment, the decrease in viability across the vacuum distillation vessel is no greater than 5 to 10%.

The viability of the microbial biomass may be measured using any suitable means. In an embodiment, the viability is measured using flow cytometry and a live/dead assay. In certain instances, the measurement of the viability of the microbial biomass in the fermentation broth is taken from the fermentation broth before entering the vacuum distillation vessel. In certain instances, the measurement of the viability of the microbial biomass in the product depleted stream is taken from the product depleted stream leaving the vacuum distillation vessel before the product depleted stream is passed to the bioreactor. In other embodiments, it may not be necessary to measure the viability of the microbial biomass at all, especially when the process has previously been demonstrated to maintain the viability of at least a portion of the microbial biomass.

In certain instances, one or more variable may be changed as a result of the viability measurement. In an embodiment, the one or more variable changed as a result of the viability measurement is selected from the group comprising: pressure, temperature, residence time, product concentration in the fermentation broth, steam feed rate, and separation medium.

In an embodiment, the product depleted stream has reduced proportions of product relative to the fermentation broth so as to prevent, or at least mitigate, accumulation of product in the fermentation broth. By preventing, or at least mitigating, accumulation of product in the fermentation broth the fermentation process may be continuous. In an embodiment, the product is recovered from a continuous fermentation process. In certain instances, the product depleted stream comprises less than 20% of the product contained in the feed stream, or less than 10% of the product contained in the feed stream, or less than 5% of the product contained in the feed stream, or less than 2.5% of the product contained in the feed stream, or less than 2% of the product contained in the feed stream, or less than 1% of the product contained in the feed stream.

In certain instances, vacuum distillation vessel provides a pressure drop over the height of the vacuum distillation vessel of less than 3.2 kPa (absolute). In certain instances, the pressure drop over the height of the vacuum distillation vessel is less than 3 kPa (absolute), less than 2.8 kPa (absolute), less than 2.6 kPa (absolute), less than 2.4 kPa (absolute), less than 2.2 kPa (absolute), less than 2 kPa (absolute), or less than 1.8 kPa (absolute).

To effectively remove the product from the fermentation broth, while maintaining microorganism viability, the vacuum distillation vessel operates at a pressure below atmospheric pressure. In an embodiment, the vacuum distillation vessel is operated at a pressure between 4 kPa (absolute) and 10 kPa (absolute), or between 4 kPa (absolute) and 10 kPa (absolute), or between 4 kPa (absolute) and 6 kPa (absolute), or between 5 kPa (absolute) and 10 kPa (absolute), or between 5 kPa (absolute) and 8 kPa (absolute), or between 5 kPa (absolute) and 7 kPa (absolute), or between 6 kPa (absolute) and 10 kPa (absolute), or between 8 kPa (absolute) and 10 kPa (absolute).

To effectively remove the product from the fermentation broth, the vacuum distillation operates at a temperature range capable of removing product, while ensuring the viability of the microorganisms. In certain instances, the product is selected from the group consisting of ethanol, acetone, and isopropanol. In an embodiment, the vacuum distillation vessel is operated at a temperature between 30° C. and 50° C. In one embodiment, the temperature is between 30° C. and 45° C., or between 37° C. and 45° C., or between 45° C. and 50° C. In various instances, the temperature is less than 37° C.

In certain instances, one or more by-products are produced by the fermentation. In certain instances, the one or more by-products are selected from the group consisting of carboxylic acids (e.g., acetic acid and lactic acid), acetone, 3-hydroxybutyrate, isobutanol, n-propanol, n-butanol, and/or 2,3-butanediol. In certain instances, the one or more by-products are not separated from the fermentation broth and are returned to the bioreactor in the product depleted stream. Due to the continuous return of by-products to the bioreactor, the amount of by-product in the fermentation may accumulate. In certain instances, it is desirable to maintain the concentration of by-products in the fermentation broth below a predetermined level. The acceptable concentration of by-products may be determined based on the tolerance of the microbe to the by-product. In certain instances, it may be desirable to provide the product depleted stream to a secondary separation means to remove one or more by-product from the product depleted stream. In certain embodiments the by-product is 2,3-butanediol and the concentration of 2,3-butanediol in the fermentation broth is maintained below 10 g/L. In certain instances, the by-product is acetic acid and the concentration of acetic acid in the fermentation broth is maintained below 10 g/L.

In certain instances, the temperature of the product depleted stream is elevated such that the product depleted stream needs to be cooled prior to being passed to the bioreactor. The temperature of the stream may have a direct effect on the viability of the microorganism. For instance, higher temperatures may result in a decrease in microorganism viability. To avoid the negative effects of increased temperature, the product depleted stream may be cooled by any suitable cooling means prior to being sent to the bioreactor. In an embodiment, the temperature of the product depleted stream is cooled to between 30° C. and 40° C. prior to being returned to the bioreactor. In an embodiment, the fermentation broth and the product depleted stream are kept below 45° C. to avoid the detrimental effects on viability. In one embodiment, the temperature is between 37° C. and 45°

C. to avoid detrimental effects. In certain instances, the temperature is dependent on the microorganism being used. The effect of temperature on microorganism viability may be heightened at higher residence times. For instance, at higher residence times, when the temperature is above optimal, the viability of the microorganisms may decrease.

In certain instances, the fermentation broth may contain proportions of gas. Gas in the fermentation broth has been shown to negatively impact the performance of the vacuum distillation vessel. This decrease in performance may be due, at least in part, on the correlation between gas in the fermentation broth and production of foam in the vacuum distillation vessel. To reduce the proportions of gas in the fermentation broth, a degassing vessel may be utilized. When utilizing a degassing vessel, the inlet for receiving the fermentation broth may be connected by piping means to the degassing vessel. The degassing vessel is operated under conditions to remove at least a portion of the gas from the fermentation broth prior to the fermentation broth being delivered to the vacuum distillation vessel.

In certain instances, the degassing vessel is operated at pressure. In certain instances, the degassing vessel is operated at any pressure less than the operating pressure of the bioreactor. In an embodiment, the degassing vessel is operated at a pressure between 0.0 kPa (gauge) and 100 kPa (gauge). In one embodiment, the degassing vessel is operated at a pressure between 0.0 (gauge) kPa and 50 kPa (gauge). In an embodiment, the degassing vessel removes substantially all of the gas from the fermentation broth. In particular embodiments, the degassing vessel removes between 0 and 100% of the gas in the fermentation broth. In certain instances, the degassing vessel removes more than 20%, more than 40%, more than 60%, or more than 80% of the gas from the fermentation broth. In certain instances, the degassing vessel removes at least a portion of carbon dioxide from the fermentation broth. In certain instances, the degassing vessel removes at least 20%, or at least 40%, or at least 60%, or at least 80% of carbon dioxide from the fermentation broth.

The process may be capable of removing product from a fermentation broth received from a bioreactor operated under conditions for fermentation of a C1-containing substrate from an industrial process. This C1-containing substrate may be sourced from one or more industrial process. In an embodiment, the industrial process is selected from the group comprising: carbohydrate fermentation, gas fermentation, cement making, pulp and paper making, steel making, oil refining and associated processes, petrochemical production, coke production, anaerobic or aerobic digestion, gasification, pyrolysis, torrefaction, natural gas extraction, oil extraction, metallurgical processes, and catalytic processes.

In certain instances, the process incorporates a distillation vessel operated at conditions to distill fermentation broth comprising ethanol, isopropanol, and water to produce a product enriched stream comprising ethanol and isopropanol and a product depleted stream comprising water. In various instances, the distillation vessel is operated at atmospheric pressure. In an embodiment, the distillation vessel passes at least a portion of the product enriched stream to the extractive distillation vessel. In instances where the distillation vessel is operated at atmospheric pressure, one or more upstream filtration technology may further be utilized to separate microbial biomass from the fermentation broth prior to being distilled. Such filtration technology may include, but is not limited to, ceramic membranes.

The fermentation broth being processed may contain any suitable microorganism. For example, the microorganism may be selected from the group comprising: *Escherichia coli, Saccharomyces cerevisiae, Clostridium acetobutylicum, Clostridium beijerinckii, Clostridium saccharbutyricum, Clostridium saccharoperbutylacetonicum, Clostridium butyricum, Clostridium diolis, Clostridium kluyveri, Clostridium pasterianium, Clostridium novyi, Clostridium difficile, Clostridium thermocellum, Clostridium cellulolyticum, Clostridium cellulovorans, Clostridium phytofermentans, Lactococcus lactis, Bacillus subtilis, Bacillus licheniformis, Zymomonas mobilis, Klebsiella oxytoca, Klebsiella pneumonia, Corynebacterium glutamicum, Trichoderma reesei, Cupriavidus necator, Pseudomonas putida, Lactobacillus plantarum*, and *Methylobacterium extorquens*. In certain instances, the microorganism may be a C1-fixing bacterium selected from the group comprising: *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kiuvi*. In an embodiment, the microorganism is a member of the genus *Clostridium*. In certain instances, the microorganism is *Clostridium autoethanogenum*.

The microorganisms may be capable of producing a variety of different products. In an embodiment, one or more products produced by the microorganisms is a low boiling fermentation product. In certain instances, the product is selected from the group consisting of ethanol, acetone, isopropanol, butanol, ketones, methyl ethyl ketone, acetone, 2-butanol, 1-propanol, methyl acetate, ethyl acetate, butanone, 1,3-butadiene, isoprene, and isobutene. In certain instances, the method is optimized based upon the product being produced. In certain instances, the product produced in the bioreactor is ethanol and isopropanol. In an embodiment, the method is optimized such that ethanol and isopropanol can be effectively removed from the fermentation broth. In certain instances, the microorganism produces at least one by-product. In one embodiment the at least one by-product is selected from the group consisting of acetic acid, lactic acid, acetone, 3-hydroxybutyrate, isobutanol, n-propanol, n-butanol, and/or 2,3-butanediol.

In various embodiments, a dehydration reactor is used either alone or alongside the extractive distillation vessel to recover product. When incorporating a dehydration reactor, at least a portion of the product enriched stream, comprising ethanol and isopropanol, is passed from a distillation vessel to the dehydration reactor. In an embodiment, the distillation vessel is a vacuum distillation vessel operated at conditions to partially vaporize a fermentation broth comprising microbial biomass, ethanol, and isopropanol, to produce the product enriched stream and a product depleted stream comprising microbial biomass. The dehydration reactor is operated under conditions to dehydrate the product enriched stream to produce a dehydrated product enriched stream comprising ethylene and propylene, and a water-rich stream. In an embodiment, at least a portion of the water-rich stream is recycled to the bioreactor.

In an embodiment, at least a portion of the product enriched stream is fed to the dehydration reactor, optionally with an inert gas such as $N_2$, pre-heated to a selected reaction temperature, and passed over a dehydration catalyst (e.g., alumina, modified alumina, silicoaluminate, modified silicoaluminate, and other catalysts) at a temperature and pressure sufficient to carry out the dehydration reactions that forms ethylene and/or propylene. The conditions depend on the catalyst used, which may be determined using methods known to those of ordinary skill in the art.

In certain instances, the dehydration reactor is operated at a temperature between 200° C. and 500° C. In various embodiments, the dehydration reactor is operated between 300° C. to 450° C., 200° C. to 450° C., or 300° C. to 500° C.

In certain instances, the dehydration reactor is operated at a pressure between 0 MPa (gauge) to 8.3 MPa (gauge). In various embodiments, the dehydration reactor is operated between 0 MPa (gauge) to 3.5 MPa (gauge) or 3.5 MPa (gauge) to 8.3 MPa (gauge).

In certain instances, the product enriched stream may be passed to the dehydration reactor at a weight hourly space velocity (WHSV) between 0.1 $h^{-1}$ to 30 $h^{-1}$. In various embodiments, the product enriched stream is passed to the dehydration reactor at a WHSV between 0.5 $h^{-1}$ to 5 $h^{-1}$, 0.1 $h^{-1}$ to 5 $h^{-1}$, 0.1 $h^{-1}$ to 5 $h^{-1}$, or 5 $h^{-1}$ to 30 $h^{-1}$.

In an embodiment, the product enriched stream comprises ethanol and/or isopropanol. In certain instances, the product enriched stream comprises 20 to 100 wt. % ethanol. In certain instances, the product enriched stream comprises 20 to 100 wt. % isopropanol. In various embodiments, the product enriched stream comprises at least 10 wt. %, at least 20 wt. %, at least 30 wt. %, at least 30 wt. %, at least 40 wt. %, at least 50 wt. %, at least 60 wt. %, at least 70 wt. %, at least 80 wt. % ethanol. In various embodiments, the product enriched stream comprises at least 10 wt. %, at least 20 wt. %, at least 30 wt. %, at least 30 wt. %, at least 40 wt. %, at least 50 wt. %, at least 60 wt. %, at least 70 wt. %, at least 80 wt. % isopropanol.

At least a portion of the dehydrated product stream may optionally be converted to at least a portion of hydrocarbon fuel. The conversion of the dehydration product stream to at least a portion of a hydrocarbon fuel may be completed through any suitable method known to those of ordinary skill in the art. In at least one embodiment, at least a portion of the dehydrated product stream is converted to at least a portion of a hydrocarbon fuel through a method comprising a two-step oligomerization process. In an embodiment, the first oligomerization process is carried out at a temperature from 40° C. to 220° C. to form a first oligomerization product. In an embodiment, the second oligomerization process oligomerizes the first oligomerization product at a temperature from 150° C. to 450° C. to form a second oligomerization product.

At least a portion of the dehydrated product stream may optionally be polymerized. Polymerization may be conducted on either the mixed ethylene and propylene stream, or separately on an ethylene-rich stream and a propylene-rich stream. In an embodiment at least a portion of the propylene is polymerized to form polypropylene. In an embodiment at least a portion of the ethylene is polymerized to form polyethylene.

DETAILED DESCRIPTION

Figure 1:
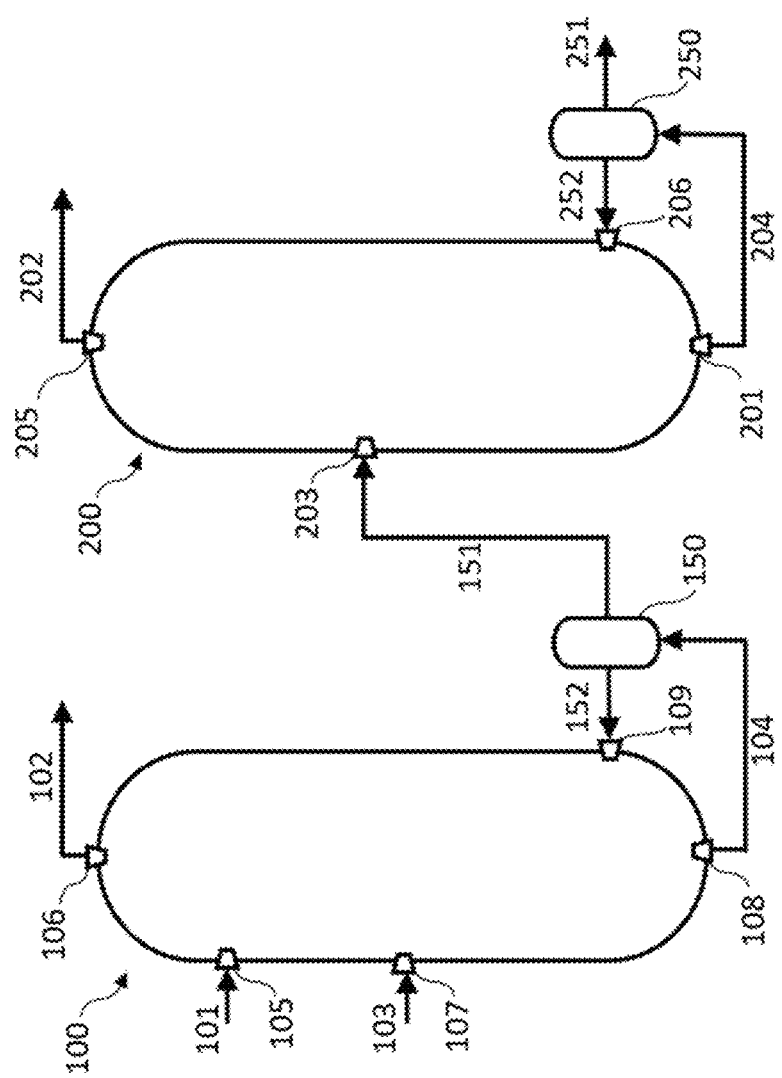
FIG. 1 is a schematic flow diagram showing an extractive distillation vessel in combination with a separation vessel, in accordance with one aspect of the disclosure.

The inventors have identified that by using an extractive distillation vessel downstream of a vacuum distillation vessel, products with close boiling points, such as ethanol and isopropanol, can be effectively recovered from a fermentation broth, containing viable microbial biomass, while ensuring the viability of the microbial biomass.

Definitions

The term "extractive distillation vessel" is intended to encompass a device for distilling components with low relative volatilities, such as ethanol and isopropanol, through use of the addition of a third component, the extractive distillation agent, to modify the relative volatility of the components. To recover the extractive distillation agent, a separation vessel is utilized downstream of the extractive distillation vessel. In an embodiment, the separation vessel receives the distillation bottoms from the extractive distillation vessel. In an embodiment, the extractive distillation vessel receives the product enriched stream from a distillation vessel. In certain instances, this distillation vessel is a vacuum distillation vessel.

The term "extractive distillation agent" is intended to encompass any component capable of modifying the relative volatility of the products. In an embodiment, the extractive distillation agent is capable of modifying the relative volatility of ethanol and isopropanol, so as to enable the separation of ethanol and isopropanol. In addition to modifying the relative volatility, the extractive distillation agent may also have a high boiling point difference between ethanol and/or isopropanol.

The term "vacuum distillation vessel" is intended to encompass a device for conducting distillation under vacuum, wherein the liquid being distilled is enclosed at a low pressure to reduce its boiling point. In an embodiment, the vacuum distillation vessel includes a separation section. In an embodiment, the liquid being distilled is fermentation broth comprising microbial biomass and at least one product. In an embodiment, at least a portion of the microbial biomass is viable. Such fermentation broth may be sourced from a bioreactor. The bioreactor may be used for fermentation of a C1-containing substrate.

The "separation section" may be composed of any suitable medium capable of providing a large surface area for vapor-liquid contact, which increases the effectiveness of the vacuum distillation column. Such separation medium is designed to provide a plurality of theoretical distillation stages. In at least one embodiment, the separation medium is a series of distillation trays. In at least one embodiment, the separation medium is composed of packing material.

"Distillation trays" or "distillation plates" and the like are intended to encompass plates and/or trays used to encourage vapor-liquid contact. Tray types include sieve, valve, and bubble cap. Sieve trays which contain holes for vapor to flow through are used for high capacity situations providing high efficiency at a low cost. Although less expensive, valve trays, containing holes with opening and closing valves, have the tendency to experience fouling due to the accumulation of material. Bubble cap trays contain caps and are the most advanced and expensive of the three trays and are highly effective in some liquid flow rate situations.

In an embodiment, the "upper tray" is any suitable boundary whereby the fermentation broth may be distributed downward to the separation medium.

In an embodiment, the "lower tray" is any suitable boundary to effectuate the transfer of the product depleted stream through the outlet in the casing.

A "theoretical distillation stage" is a hypothetical zone in which two phases, such as the liquid and vapor phases of a substance, establish an equilibrium with each other. The performance of many separation processes depends on having a series of theoretical distillation stages. The performance of a separation device, such as a vacuum distillation vessel, may be enhanced by providing an increased number of stages. In an embodiment, the separation medium includes a sufficient number of theoretical distillation stages to effectively remove at least one product from the fermentation broth. In an embodiment, the separation medium includes multiple theoretical distillation stages.

The term "fermentation broth" or "broth" is intended to encompass the mixture of components including the nutrient media, the culture of one or more microorganisms, and the one or more products. It should be noted that the term microorganism and the term bacteria are used interchangeably throughout the document.

"Nutrient media" or "nutrient medium" is used to describe microbial growth media. Generally, this term refers to a media containing nutrients and other components appropriate for the growth of a microbial culture. The term "nutrient" includes any substance that may be utilized in a metabolic pathway of a microorganism. Exemplary nutrients include potassium, B vitamins, trace metals, and amino acids.

In an embodiment, the fermentation broth is sent from a "bioreactor" to the vacuum distillation vessel. The term "bioreactor" includes a fermentation device consisting of one or more vessels and/or towers or piping arrangements, which includes the Continuous Stirred Tank Reactor (CSTR), Immobilized Cell Recycles (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor may be adapted to receive a gaseous substrate comprising CO or $CO_2$ or $H_2$ or mixtures thereof. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

"Gaseous substrates comprising carbon monoxide" include any gas which contains carbon monoxide. The gaseous substrate will typically contain a significant proportion of CO, in an embodiment at least about 5% to about 100% CO by volume.

While it is not necessary for the substrate to contain any hydrogen, the presence of $H_2$ should not be detrimental to product formation in accordance with methods of the disclosure. In particular embodiments, the presence of hydrogen results in improved overall efficiency of alcohol production. For example, in particular embodiments, the substrate may comprise an approx. 2:1, or 1:1, or 1:2 ratio of $H_2$:CO. In one embodiment, the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment, the substrate comprises less than or equal to about 20% $CO_2$ by volume. In particular embodiments, the substrate comprises less than or equal to about 15% $CO_2$ by volume, less than or equal to about 10% $CO_2$ by volume, less than or equal to about 5% $CO_2$ by volume or substantially no $CO_2$.

The use of a vacuum distillation vessel with a bioreactor may increase the efficiency of the fermentation process. The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

Unless the context requires otherwise, the phrases "fermenting", "fermentation process" or "fermentation reaction" and the like, as used herein, are intended to encompass both the growth phase and product biosynthesis phase of the microorganisms.

The fermentation process may be described as either "batch" or "continuous". "Batch fermentation" is used to describe a fermentation process where the bioreactor is filled with raw material, i.e. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. In an embodiment, the vacuum distillation vessel removes the product from a "continuous fermentation" process.

A "microorganism" or "microbe" is a microscopic organism, especially a bacterium, archea, virus, or fungus. The microorganism of the disclosure is typically a bacterium. As used herein, recitation of "microorganism" should be taken to encompass "bacterium."

"Viability" or "viability of the microbial biomass" and the like refers to the ratio of microorganisms that are alive, capable of living, developing, or reproducing to those that are not. For example, viable microbial biomass in a vacuum distillation vessel may refer to the ratio of live/dead microorganisms within the vacuum distillation vessel. The disclosure may be designed so that the viability of the microbial biomass is maintained at a minimum viability. In at least one embodiment, the viability of the microbial biomass is at least about 85%. In an embodiment, the viability of the microbial biomass is at least 20%, or at least 25%, or at least 30%, or at least 40%, 50%, or at least 60%, or at least 70%, or at least 75%, or at least 80%, or at least 85%, or at least 90%. In at least one embodiment, the viable microbial biomass is returned from the vacuum distillation vessel back to the bioreactor.

"Effective rate of product recovery" and the like refers to the rate at which product can be recovered from the fermentation broth so as to prevent, or at least mitigate, the toxic and/or inhibitory effects associated with product accumulation. The disclosure may be designed so that the effective rate of product recovery is such that the viability of the microbial biomass is maintained above a desired threshold. The disclosure may be designed so that the level of product concentration in the broth is kept below a desired threshold. For example, the disclosure may be designed such that the combined ethanol and isopropanol concentration in the fermentation broth is kept below 40 g/L. In certain instances, the combined ethanol and isopropanol concentration in the fermentation broth is kept between 25 to 35 g/L. In particular instances, the combined ethanol and isopropanol concentration in the fermentation broth is less than 30 g/L, less than 35 g/L, or less than 38 g/L. In an embodiment, the combined ethanol and isopropanol concentration in the fermentation broth is less than the concentration that may result in inhibition of the microorganism. In particular instances, the inhibition may be dependent on the microorganism being used and the product being produced.

The vacuum distillation vessel may pass the product depleted stream to a "cooling means" prior to the product depleted stream being passed to the bioreactor. The term "cooling means" may describe any suitable device or process capable of reducing the temperature of the product depleted stream.

The microorganisms in the bioreactor may be modified from a naturally-occurring microorganism. A "parental microorganism" is a microorganism used to generate a microorganism of the disclosure. The parental microorganism may be a naturally-occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism. In one embodiment, the parental microorganism is *Clostridium autoethanogenum, Clostridium ljungdahlii,* or *Clostridium ragsdalei.* In one embodiment, the parental microorganism is *Clostridium autoethanogenum* LZ1561, which was deposited on Jun. 7, 2010, with Deutsche Sammlung von Mikroorganismen and Zellkulturen GmbH (DSMZ) located at InhoffenstraB 7B, D-38124 Braunschwieg, Germany on Jun. 7, 2010, under the terms of the Budapest Treaty and accorded accession number DSM23693. This strain is described in International Patent Application No. PCT/NZ2011/000144, which published as WO 2012/015317.

"Wood-Ljungdahl" refers to the Wood-Ljungdahl pathway of carbon fixation as described, i.e., by Ragsdale, Biochim Biophys Acta, 1784: 1873-1898, 2008. "Wood-Ljungdahl microorganisms" refers, predictably, to microorganisms containing the Wood-Ljungdahl pathway. Generally, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (i.e., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, $CO_2$, $CH_4$, $CH_3OH$, or $CH_2O_2$. In an embodiment, the C1-carbon source comprises one or both of CO and $CO_2$. A "C1-fixing microorganism" is a microorganism that has the ability to produce one or more products from a C1-carbon source. Typically, the microorganism of the disclosure is a C1-fixing bacterium.

An "anaerobe" is a microorganism that does not require oxygen for growth. An anaerobe may react negatively or even die if oxygen is present above a certain threshold. However, some anaerobes are capable of tolerating low levels of oxygen (i.e., 0.000001-5% oxygen). Typically, the microorganism of the disclosure is an anaerobe.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, Biochim Biophys Acta, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, NY, 2006). All naturally occurring acetogens are C1-fixing, anaerobic, autotrophic, and non-methanotrophic. Typically, the microorganism of the disclosure is an acetogen.

An "ethanologen" is a microorganism that produces or is capable of producing ethanol. Typically, the microorganism of the disclosure is an ethanologen.

An "autotroph" is a microorganism capable of growing in the absence of organic carbon. Instead, autotrophs use inorganic carbon sources, such as CO and/or $CO_2$. Typically, the microorganism of the disclosure is an autotroph.

A "carboxydotroph" is a microorganism capable of utilizing CO as a sole source of carbon and energy. Typically, the microorganism of the disclosure is a carboxydotroph.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

"Substrate" refers to a carbon and/or energy source for the microorganism of the disclosure. Typically, the substrate is gaseous and comprises a C1-carbon source, for example, CO, $CO_2$, and/or $CH_4$. In an embodiment, the substrate comprises a C1-carbon source of CO or CO+$CO_2$. The substrate may further comprise other non-carbon components, such as $H_2$, $N_2$, or electrons.

The term "co-substrate" refers to a substance that, while not necessarily being the primary energy and material source for product synthesis, can be utilized for product synthesis when added to another substrate, such as the primary substrate.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a by-product of an industrial process. In certain embodiments, the industrial process is selected from the group consisting of carbohydrate fermentation, gas fermentation, cement making, pulp and paper making, steel making, oil refining and associated processes, petrochemical production, coke production, anaerobic or aerobic digestion, gasification, pyrolysis, torrefaction, natural gas extraction, oil extraction, metallurgical processes, and catalytic processes. In these embodiments, the substrate and/or C1-carbon source may be captured from the industrial process before it is emitted into the atmosphere, using any convenient method.

The microorganism of the disclosure may be cultured with the gas stream to produce one or more products. For instance, the microorganism of the disclosure may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498).

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. The list of potential fermentation products produced by the microorganism are listed above, which may exclude microbial biomass. The microorganism of the disclosure may be engineered to produce products at a certain selectivity or at a minimum selectivity. In one embodiment, a target product accounts for at least about 5%, 10%, 15%, 20%, 30%, 50%, 75%, or 95% of all fermentation products produced by the microorganism of the disclosure. In one embodiment, the target product accounts for at least 10% of all fermentation products produced by the microorganism of the disclosure, such that the microorganism of the disclosure has a selectivity for the target product of at least 10%. In another embodiment, the target product accounts for at least 30% of all fermentation products produced by the microorganism of the disclosure, such that the microorganism of the disclosure has a selectivity for the target product of at least 30%. In various instances, the target products are ethanol and isopropanol. In certain instances, the target product is ethanol. In certain instances, the target product is isopropanol.

The vacuum distillation vessel is capable of recovering one or more "low boiling fermentation product." A "low boiling fermentation product" is a product that is more volatile than water. These products may include, but are not limited to, ethanol, acetone, isopropanol, butanol, ketones, methyl ethyl ketone, 2-butanol, 1-propanol, methyl acetate, ethyl acetate, butanone, 1,3-butadiene, isoprene, and isobutene.

The culture is generally maintained in an aqueous culture medium that contains nutrients, vitamins, and/or minerals sufficient to permit growth of the microorganism. In an embodiment the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, one embodiment is to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. In one embodiment the fermentation may be operated at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently, the capital cost of the fermentation equipment.

DESCRIPTION

Extractive distillation has been found to effectively separate close-boiling products, such as ethanol boiling at 78.4° C. and isopropanol boiling at 82.4° C., produced from the fermentation of a C1-containing gaseous substrate. Extractive distillation is achieved through processing of a product enriched stream, comprising ethanol and isopropanol, in the presence of an extractive distillation agent. In an embodiment, the extractive distillation vessel is used in combination with a distillation vessel and a separation vessel. In an embodiment, the distillation vessel is a vacuum distillation vessel operated under conditions to ensure the viability of the microorganisms contained in the fermentation broth. By combining extractive distillation with vacuum distillation close-boiling products can be separated while ensuring the viability of the microorganisms contained in the fermentation broth.

It was found by the inventors that by combining a distillation vessel with an extractive distillation vessel and a separation vessel, ethanol and isopropanol can be effectively recovered and separated from fermentation broth all while preserving the viability of the microorganisms within the fermentation broth. Additionally, through the optimal configuration of these vessels, the unwanted by-products produced are reduced, energy is conserved, and production of specific target products are maximized. For example, by recycling one or more product, such as ethanol or acetone, the fermentation process may produce increased amounts of a specific target product, such as isopropanol.

FIG. 1 shows an extractive distillation vessel 100 in combination with a separation vessel 200. The extractive distillation vessel 100 is configured to receive a product enriched stream 103 and an extractive distillation agent 101 to produce an overhead product 102 and distillation bottoms 104. In an embodiment, the inlet 107 for receiving the product enriched stream 103 is below the inlet 105 for receiving the extractive distillation agent 101. In an embodiment the overhead product 102 exits the extractive distillation vessel 100 via an outlet 106 above the inlet 101 for receiving the extractive distillation agent 101. The inventors have found that by utilizing particular extractive distillation agents 101 the location for the recovery of certain products can be controlled.

To recover ethanol in the overhead product 102 the extractive distillation agent 101 is may be selected from the group consisting of alpha-pinene, beta-pinene, methyl isobutyl ketone, limonene, alpha-phellandrene, alpha-terpinene, myrcene, carane, p-mentha-1,5-diene, butyl ether, 1-methoxy-2-propanol, n-butyl acetate, n-amyl acetate, benzyl acetate, ethylene glycol ethyl ether acetate, methyl acetoacetate, ethylene glycol diacetate, 2-butoxyethyl acetate, methyl butyrate, ethyl propionate, ethyl n-valerate, butyl benzoate, ethyl benzoate, pyridine, N,N-dimethyl aniline, o-sec.butyl phenol, 3-isopropyl phenol, 2,6-dimethyl phenol, o-tert.butyl phenol, 4-ethyl phenol, diethyl phthalate, diisooctyl phthalate, dimethyl adipate, glycerine triacetate, diethyl malonate, dimethyl glutarate, tetrahydrofuran, ethylene glycol phenyl ether, dipropylene glycol methyl ether acetate, diethylene glycol hexyl ether, propoxypropanol, butoxypropanol, p-xylene glycol dimethyl ether, diethylene glycol t-butyl ether methyl ether, triethylene glycol diacetate, anisole, phenetole, phenyl ether, 1,2-methylenedioxybenzene, isophorone, ethyl-3-ethoxypropionate, tetraethylorthosilicate, 2-hydroxyacetophenone, 1,1,1-trichloroethane, tetrachloroethylene, 2,2,2-trichloroethanol, m-dichlorebenzene, chlorobenzene, 2,6-dichlorotoluene, 1-chlorohexane, diethylene glycol, dimethyl sulfoxide, dimethylformamide, sulfolane, isophorone, 2-pyrrolidinone, 1-methyl-2pyrrolindinone, isodecyl alcohol, cyclododecanol, benzyl alcohol, 1-dodecanol, tridecyl alcohol, phenethyl alcohol, cyclohexanol, cyclopentanol, 2-nitropropane, 1-nitropropane, nitro-ethane, nitromethane, 3-nitrotoluene, 2-nitrotoluene, triacetin, 3-nitro-o-xylene, 1,4-dioxane, isobutyl acetate, ethyl butyrate, isoamyl formate, methyl caproate, ethyl caproate, propyl caproate, 1-methoxy-2-propanol acetate, isobutyl isobutyrate, hexyl acetate, ethyl isobutyrate, propyl butyrate, isobutyl butyrate, isobornyl acetate, 1,3-dioxolane, nitrobenzene, butyl butyrate, 4-methyl-2-pentanone, and polyethylene glycol 400.

To recover isopropanol in the overhead product 102 the extractive distillation agent 101 may be selected from the group consisting of ethyl benzene, toluene, p-xylene, heptane, phenol, and 2-tert-butyl phenol.

In an embodiment, the extractive distillation agent 101 is added to the extractive distillation vessel 100 at least at a 5:1 extractive distillation agent to alcohol ratio. When recovering ethanol in the overhead product 102, the ratio of extractive distillation agent to alcohol is in terms of extractive distillation agent to ethanol. When recovering isopropanol in the overhead product 102, the ratio of extractive distillation agent to alcohol is in terms of extractive distillation agent to isopropanol. In an embodiment the extractive distillation agent 101 is added at an optimal ratio so as to modify the relative volatility between the ethanol and the isopropanol in the product enriched stream 103. In certain instances, the extractive distillation agent is added at least at a 5:1, 10:1, 20:1, or 40:1 extractive distillation agent to alcohol ratio.

To effectuate the separation of ethanol from isopropanol a reboiler 150 is used by the extractive distillation vessel 100. The reboiler 150 is provided so as to direct a vapor stream to the extractive distillation vessel 100. This vapor stream is directed through piping means 152 from the reboiler 150 to an inlet 109 in the extractive distillation vessel 100. The vapor stream enters the extractive distillation vessel 100 and rises upward through the extractive distillation vessel 100. The reboiler 150 may create the vapor stream by heating the distillation bottoms 104 sent from an outlet 108 in the extractive distillation vessel 100.

At least a portion of the product 103 not recovered in the overhead product 102 is recovered in the distillation bottoms 104 along with the extractive distillation agent 101. When ethanol is recovered in the overhead product 102, the distillation bottoms 104 comprise isopropanol and the extractive distillation agent 101. When isopropanol is recovered in the overhead product 102, the distillation bottoms 104 comprise ethanol and the extractive distillation agent. To effectuate the separation of the alcohol and the extractive distillation agent 101 in the distillation bottoms, at least a portion of the distillation bottoms 104 are passed from the reboiler 150 through piping means 151 to an inlet 203 in the separation vessel 200.

The separation vessel 200 separates the extractive distillation agent 101 from the alcohol in the distillation bottoms 104 through use of a reboiler 250. The reboiler 250 is provided so as to direct a vapor stream to the separation vessel 200. This vapor stream is directed through piping means 252 from the reboiler 250 to the inlet 206 in the separation vessel 200. The vapor stream enters the separation vessel 200 and rises upward through the separation vessel 200. The reboiler 250 may create the vapor stream by heating the distillation bottoms 204 from sent from an outlet 201 in the separation vessel 200.

At least a portion of the alcohol in the distillation bottoms 104 is recovered in the overhead product 202 through an outlet 205 in the separation vessel 200. In instances where ethanol is recovered in the overhead product 102 of the extractive distillation vessel 100, the overhead product 202 in the separation vessel 200 is enriched in isopropanol. In instances where isopropanol is recovered in the overhead product 102 of the extractive distillation vessel 100, the overhead product 202 in the separation vessel 200 is enriched in ethanol. In an embodiment, extractive distillation vessel 100 and the separation vessels 200 are configured to reduce waste. In certain instances, the extractive distillation agent 251 remaining in the distillation bottoms 204 is removed from the reboiler 250 and is recycled back to the extractive distillation column 100.

In an embodiment, the extractive distillation vessel 100 and the separation vessel 200 are utilized in combination with a distillation vessel. The distillation vessel may, in certain instances, be operated at vacuum.

Figure 2:
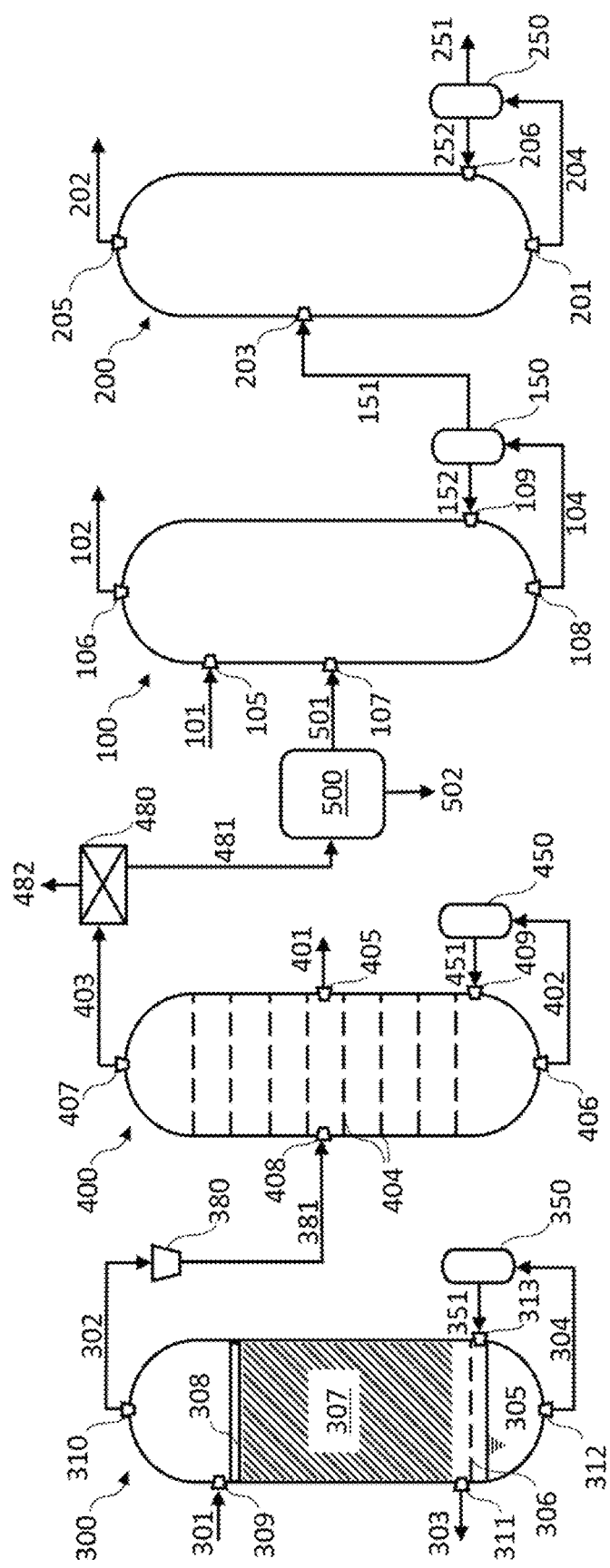
FIG. 2 is a schematic flow diagram showing a vacuum distillation vessel upstream of the extractive distillation vessel and the separation vessel, in accordance with one aspect of the disclosure.

FIG. 2 shows a vacuum distillation vessel 300 upstream of the extractive distillation vessel 100. The vacuum distillation vessel 300 may be configured for recovering product from a fermentation broth 301, comprising microbial biomass, ethanol, and isopropanol, the fermentation broth being delivered from a bioreactor. To recover product from the fermentation broth 301, the vacuum distillation vessel 300 partially vaporizes the fermentation broth 301 and produces a product enriched stream 302 and a product depleted stream 303. In an embodiment, at least a portion of the product depleted stream 303 is passed back to the bioreactor through an outlet 311. The product depleted stream 303 may comprise microbial biomass. The product enriched stream 302 may comprise ethanol and isopropanol. In an embodiment, at least a portion of the product enriched stream 302 is passed from an outlet 310 in the vacuum distillation vessel 310 to an inlet 107 in the extractive distillation vessel 100.

The vacuum distillation vessel 300 is configured to receive fermentation broth 301 from the bioreactor via an inlet 309 in the vacuum distillation vessel 300. The vacuum distillation vessel 300 comprises a separation section 307, the separation section 307 is bound above by an upper tray 308 and below by a lower tray 306. The separation section 307 may be comprised of a series of distillation trays and/or packing material. The vacuum distillation vessel 100 is designed in a way to increase the recovery of product from the fermentation broth 301. The outlet 310 for transferring the product enriched stream 302 is elevated relative to the inlet 309 for receiving the fermentation broth 301. The inlet 309 for receiving the fermentation broth 301 being elevated relative to the upper tray 308, the outlet 306 for transferring the product depleted stream 303 being elevated relative to the lower tray 306.

In an embodiment, a reboiler 350 is used by the vacuum distillation vessel 300. The reboiler 350 is provided so as to direct a vapor stream to the vacuum distillation vessel 300. The vapor stream is created through the use of the liquid bottoms 305 of the vacuum distillation vessel 300, which exit the vacuum distillation vessel 300 through an outlet 312 and is fed to the reboiler 350 via piping means 304. This vapor stream is directed through piping means 351 from the reboiler 350 to an inlet 313 in the vacuum distillation vessel 300. The vapor stream enters the vacuum distillation vessel 300 and rises upward through the vacuum distillation vessel 300.

The vacuum distillation vessel 100 is designed such that the vacuum distillation vessel 300 can process fermentation broth at a given feed rate. The feed rate is defined in terms of bioreactor volumes of fermentation broth per hour. In an embodiment, the vacuum distillation vessel 300 is designed such that the feed rate is between 0.05 to 0.5.

The vacuum distillation vessel 300 is designed such that the fermentation broth 301 defines a residence time. The residence time is defined in terms of the amount of time the fermentation broth 301 is within the vacuum distillation vessel 300. The fermentation broth 301 is deemed to be within the vacuum distillation vessel 300 when the fermentation broth 301 enters through the inlet 309. The fermentation broth 301 is deemed to be out of the vacuum distillation vessel 300 when the fermentation broth 301 exits through the outlet 311. In an embodiment, the residence time is between 0.5 and 15 minutes. In various embodiments, the residence time is between 0.5 and 12 minutes, 0.5 and 9 minutes, 0.5 and 6 minutes, 0.5 and 3 minutes, 2 and 15 minutes, 2 and 12 minutes, 2 and 9 minutes, or 2 and 6 minutes. In at least one embodiment, the residence time is less than 15 minutes, less than 12 minutes, less than 9 minutes, less than 6 minutes, less than 3 minutes, less than 2 minutes, or less than 1 minute to ensure the viability of the microorganisms.

The given residence time may depend, at least in part, on the type of separation medium 307 within the vacuum distillation vessel 300. In at least one embodiment, the separation medium 307 is defined by a series of distillation trays. In an embodiment, a separation medium 307 is provided such that a sufficient number of theoretical distillation stages are provided to recover product. In an embodiment, the separation medium 307 provides multiple theoretical distillation stages. In other embodiments, the separation medium 307 provides a minimum number of theoretical distillation stages, for example, more than 3 theoretical distillation stages, more than 4 theoretical distillation stages, more than 5 theoretical distillation stages, or more than 6 theoretical distillation stages.

The vacuum distillation vessel 300 is designed so as to effectively recover product in the fermentation broth 301 and prevent product accumulation in the bioreactor. In an embodiment, the product depleted stream 303 has reduced proportions of product such that product accumulation is effectively reduced or eliminated. In at least one embodiment, the product depleted stream 303 comprises less than 10% of the product contained in the fermentation broth 301 feed stream. In certain embodiments, the product depleted stream 303 comprises less than 20% of the product contained in the fermentation broth 301 feed stream. In particular instances, the product depleted stream 303 comprises between 12.5 and 5% of the product contained in the fermentation broth 301 feed stream. In at least one embodiment, the product being recovered is ethanol and isopropanol.

The vacuum distillation vessel 300 is designed so as to ensure the viability of the microorganisms while providing product recovery. In embodiments, the product depleted stream 303 comprises microbial biomass that is at least 20 percent viable, or at least 25 percent viable, or at least 50 percent viable. To ensure the viability of the microorganisms, the vacuum distillation vessel 300 is designed such that the pressure drop over the height of the vacuum distillation vessel 300, the pressure within the vacuum distillation vessel 300, and the temperature within the vacuum distillation vessel 300 are closely controlled.

The vacuum distillation vessel 300 is designed so as to enable the transfer of a product enriched stream 302 and a product depleted stream 303. In certain instances, the product depleted stream 303 may have higher than acceptable temperature, and thus may require cooling prior to being transferred to the bioreactor. To effectuate cooling, a cooling means may be provided. In an embodiment, the temperature of the product depleted stream 303 is between 30° C. and 40° C. before being sent to the bioreactor.

In some instances, the fermentation broth 301 may have higher than acceptable proportions of gas, and thus may require degassing prior to being transferred to the vacuum distillation vessel 300. To effectuate degassing, a degassing vessel may be provided. In an embodiment, the degassing vessel is a cyclonic degasser.

In certain instances, the product enriched stream 302 may comprise one or more by-product and higher than optimal amount of water. In instances where the product enriched stream 302 comprises by-products and/or higher than optimal amounts of water, one or more additional process may be utilized. To effectuate the removal of by-products and/or water from the product enriched stream 302, the product enriched stream 302 may be sent from the vacuum distillation vessel 300 to an inlet 408 in a rectification column 400. Prior to being sent to the rectification column 400, the product enriched stream 302 may be sent to one or more compression vessel 380, which may utilize mechanical vapor recompression technology, to compress the product enriched stream 302. The compressed product enriched stream 381 is processed by the rectification column 400 to remove excess water and/or by-products 401. One or more of the by-products 401 may be removed through a side draw via an outlet 405 in the rectification column 400. In an embodiment, 3-hydroxybutyrate, isobutanol, n-propanol, and/or n-butanol are removed through the side draw in the rectification column. In an embodiment, the rectification column 400 comprises a separation section 404. The separation section 404 may be comprised of a series of distillation trays and/or packing material to facilitate the removal of excess water and/or by-products from the product enriched stream.

In an embodiment, a reboiler 450 is used by the rectification column 400. The reboiler 450 is provided so as to direct a vapor stream to the rectification column 400. The vapor stream is created through the use of the bottoms of the rectification column 400, which exits the rectification column 400 through an outlet 406 and is fed to the reboiler 450 via piping means 402. This vapor stream is directed through piping means 451 from the reboiler 450 to an inlet 409 in the rectification column 400. The vapor stream enters the rectification column 400 and rises upward through the rectification column 400.

In some circumstances, portions of the by-products in the product enriched stream 302 may end up in the overhead product 403 exiting the outlet 407 in the rectification column 400. To further separate by-products 481 and to control the temperature of the product enriched stream 302 a heat exchanger 480 may be utilized. In an embodiment, the heat exchanger 480 is operated at a pressure of least at 100 kPa (absolute) and a temperature at of at least 70° C. In one or more embodiments, the by-product removed by the heat exchanger 480 comprises acetone. This acetone may be in vapor form. To further remove water from the product enriched stream 302, the treated product enriched stream 481 may be sent to one or more dehydration membrane system 500 to remove excess water 502 from the product enriched stream 302. In an embodiment, the dehydrated product enriched stream 501 is sent to an extractive distillation vessel 100 to facilitate the separation of ethanol and isopropanol.

In certain instances, a dehydration reactor may be used either alongside or in replacement of the extractive distillation vessel.

Figure 3:
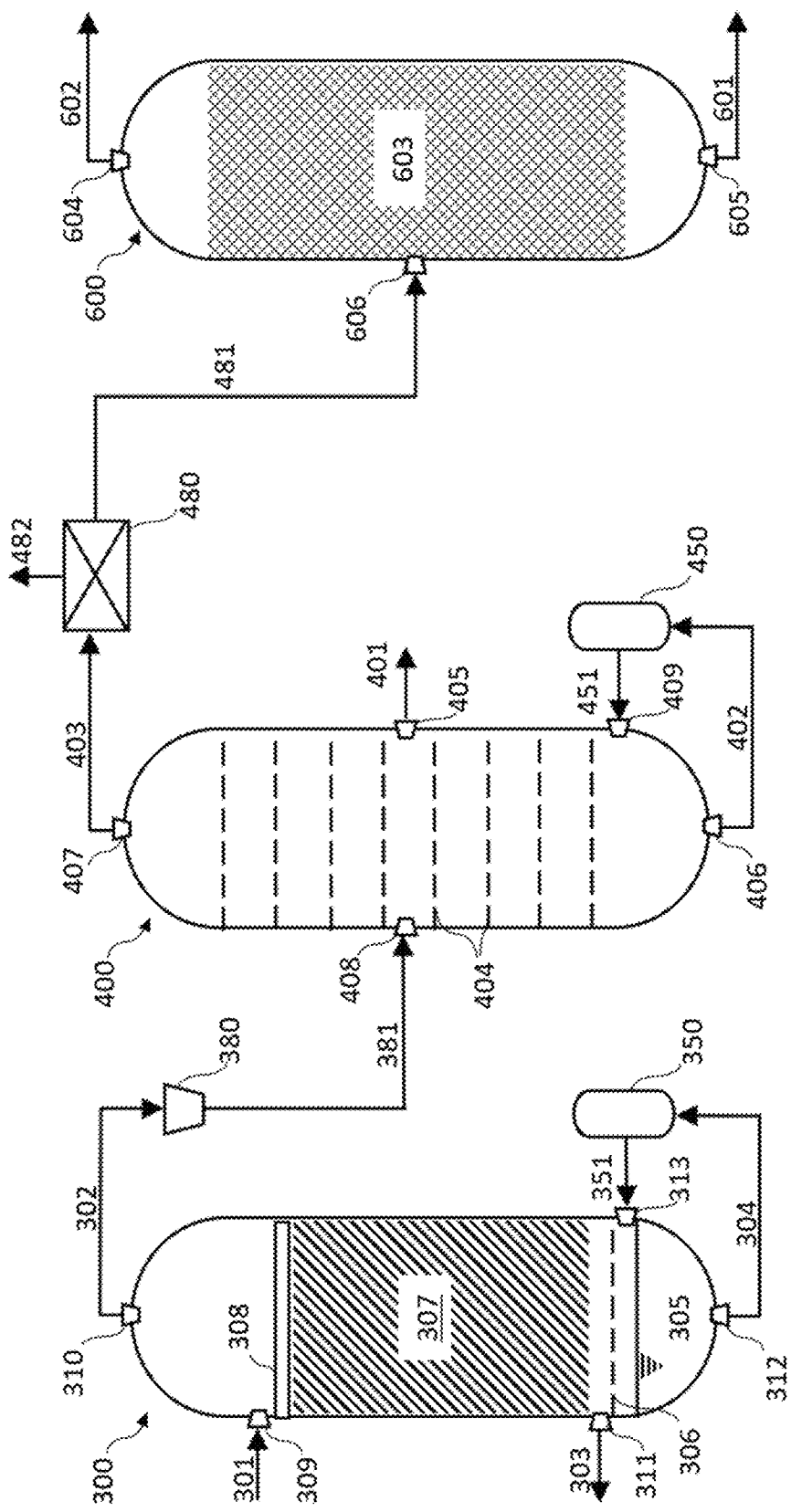
FIG. 3 is a schematic flow diagram showing a vacuum distillation vessel in combination with a dehydration reactor, in accordance with one aspect of the disclosure.

FIG. 3 shows a vacuum distillation vessel 300 upstream of a dehydration reactor 600. In various embodiments, the distillation vessel 300 is operated at atmospheric pressure. When incorporating a dehydration reactor 600, the distillation vessel 300 is configured to pass at least a portion of the product enriched stream 302, comprising ethanol and isopropanol, to the dehydration reactor 600. In certain instances, a rectification column 400 may be used upstream of the dehydration reactor 600 and downstream of the vacuum distillation vessel 300. In various instances, at least a portion of the product enriched stream 302 is passed to a heat exchanger 480 to heat the product enriched stream 302 prior to being sent dehydration reactor 600. The heated product enriched stream 481 enters the dehydration reactor 600 through an inlet 606. The diameter, length, and volume of the catalyst 603 in the dehydration reactor are designed for optimum temperature profile and residence time for the product enriched stream 481. Typically, the dehydration reactor 600 is operated at a temperature between 200° C. and 500° C. and a pressure from 0 MPa (gauge) to 8.3 MPa (gauge), to sufficiently dehydrate the product enriched stream 481 to produce a dehydrated product stream 602, comprising ethylene and propylene, and a water rich stream 601. In an embodiment, the dehydrated product stream 602 exits the dehydration reactor 600 at the outlet 604, and the water rich stream 601 exits the dehydration reactor 600 at the outlet 605.

The dehydration reactor 600 may be configured to receive the product enriched stream 481 at a suitable rate. Typically, the product enriched stream 481 is fed to the dehydration reactor 600 at a weight hourly space velocity between 0.1 $h^{-1}$ to 30 $h^{-1}$. The weight hourly space velocity of the product enriched stream 481 may correlate with the amount of catalyst 603 utilized by the dehydration reactor 600. The dehydration reactor 600 may utilize at least one catalyst 603 selected from the group consisting of alumina, modified alumina, crystalline or amorphous silicoaluminate, and modified silicoaluminate such that the ethanol and isopropanol in the product enriched stream 481 can be co-dehydrated. In certain instances, at least a portion of the dehydrated product stream 602 is further converted to at least a portion of hydrocarbon fuel. In certain instances, at least a portion of the dehydrated product stream 602 is polymerized to produce polypropylene and polyethylene. Prior to being polymerized or further converted to produce at least a portion of a hydrocarbon fuel, the dehydrated product stream 602 may be separated into an ethylene rich stream and a propylene rich stream. The separation of the dehydrated product stream 602, comprising ethylene and propylene, is more easily achievable than the initial product enriched stream 481, comprising ethanol and isopropanol, due to the greater difference in boiling points between ethylene and propylene than that of ethanol and isopropanol. Propylene boing at −47.6° C. and ethylene boiling at −103.7° C., with a difference of 56.1° C. Whereas ethanol boils at 78.4° C. and isopropanol boils at 82.4° C., with a difference of 4° C. Effective separation of the dehydrated product enriched stream 602 can be achieved through the use of cryogenic distillation technology.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavor in any country.

The use of the terms "a" and "an" and "the" and similar referents in the context of describing the disclosure (especially in the context of the following claims) are to be construed to cover both the singular and the plural unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein is merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

A first embodiment is a method for recovering product from a fermentation broth, the method comprising:
 a. passing a fermentation broth comprising microbial biomass, ethanol, and isopropanol from a bioreactor to a vacuum distillation vessel;
 b. partially vaporizing the fermentation broth to produce a product enriched stream, the product enriched stream comprising ethanol and isopropanol, and a product depleted stream, the product depleted stream comprising microbial biomass;
 c. passing at least a portion of the product depleted stream back to the bioreactor;
 d. passing at least a portion of product enriched stream to an extractive distillation vessel; and
 e. distilling the product enriched stream in the extractive distillation vessel in the presence of an extractive distillation agent to obtain an overhead product and distillation bottoms, wherein:
  i. at least a portion of the ethanol is recovered in the overhead product and at least a portion of the isopropanol is recovered in the distillation bottoms; or
  ii. at least a portion of the isopropanol is recovered in the overhead product and at least a portion of the ethanol is recovered in the distillation bottoms The method of the first embodiment wherein at least a portion of the ethanol is recovered in the overhead product and at least a portion of the isopropanol is recovered in the distillation bottoms; and wherein the extractive distillation agent comprises at least one material selected from the group consisting of alpha-pinene, beta-pinene, methyl isobutyl ketone, limonene, alpha-phellandrene, alpha-terpinene, myrcene, carane, p-mentha-1,5-diene, butyl ether, 1-methoxy-2-propanol, n-butyl acetate, n-amyl acetate, benzyl acetate, ethylene glycol ethyl ether acetate, methyl acetoacetate, ethylene glycol diacetate, 2-butoxyethyl acetate, methyl butyrate, ethyl propionate, ethyl n-valerate, butyl benzoate, ethyl benzoate, pyridine, N,N-dimethyl aniline, o-sec.butyl phenol, 3-isopropyl phenol, 2,6-dimethyl phenol, o-tert.butyl phenol, 4-ethyl phenol, diethyl phthalate, diisooctyl phthalate, dimethyl adipate, glycerine triacetate, diethyl malonate, dimethyl glutarate, tetrahydrofuran, ethylene glycol phenyl ether, dipropylene glycol methyl ether acetate, diethylene glycol hexyl ether, propoxypropanol, butoxypropanol, p-xylene glycol dimethyl ether, diethylene glycol t-butyl ether methyl ether, triethylene glycol diacetate, anisole, phenetole, phenyl ether, 1,2-methylenedioxybenzene, isophorone, ethyl-3-ethoxypropionate, tetraethylorthosilicate, 2-hydroxyacetophenone, 1,1,1-trichloroethane, tetrachloroethylene, 2,2,2-trichloroethanol, m-dichlorebenzene, chlorobenzene, 2,6-dichlorotoluene, 1-chlorohexane, diethylene glycol, dimethyl sulfoxide, dimethylformamide, sulfolane, isophorone, 2-pyrrolidione, 1-methyl-2pyrrolindinone, isodecyl alcohol, cyclododecanol, benzyl alcohol, 1-dodecanol, tridecyl alcohol, phenethyl alcohol, cyclohexanol, cyclopentanol, 2-nitropropane, 1-nitropropane, nitro-ethane, nitromethane, 3-nitrotoluene, 2-nitrotoluene, triacetin, 3-nitro-o-xylene, 1,4-dioxane, isobutyl acetate, ethyl butyrate, isoamyl formate, methyl caproate, ethyl caproate, propyl caproate, 1-methoxy-2-propanol acetate, isobutyl isobutyrate, hexyl acetate, ethyl isobutyrate, propyl butyrate, isobutyl butyrate, isobornyl acetate, 1,3-dioxolane, nitrobenzene, butyl butyrate, 4-methyl-2-pentanone, and polyethylene glycol 400.

The method of the first embodiment wherein at least a portion of the isopropanol is recovered in the overhead product and at least a portion of the ethanol is recovered in the distillation bottoms; and wherein the extractive distillation agent comprises at least one material selected from the group consisting of ethyl benzene, toluene, p-xylene, heptane, phenol, and 2-tert-butyl phenol.

The method of the first embodiment wherein the product enriched stream is passed to a rectification column prior to being passed to the extractive distillation vessel.

The method of the first embodiment wherein the extractive distillation agent is added to the extractive distillation vessel at least at a 5:1 extractive distillation agent to isopropanol ratio or at least a 5:1 extractive distillation agent to ethanol ratio.

The method of the first embodiment wherein the fermentation broth further comprises one or more by-product selected from the group consisting of acetic acid, acetone, 3-hydroxybutyrate, isobutanol, n-propanol, n-butanol, and/or 2,3-butanediol. The method of the first embodiment wherein at least a portion of at least one by-product is removed through a side draw. The method of the first embodiment wherein at least a portion of the 3-hydroxybuterate, isobutanol, n-propanol, and/or n-butanol are removed through a side draw.

The method of the first embodiment wherein the fermentation broth further comprises acetone, at least a portion of the acetone being recycled to the bioreactor.

The method of the first embodiment wherein the extractive distillation vessel is heat integrated.

The method of the first embodiment, further comprising: passing the distillation bottoms to a separation vessel to produce an isopropanol-enriched stream or an ethanol-enriched stream; and an extractive distillation agent enriched stream; and passing at least a portion of the extractive distillation agent enriched stream to the extractive distillation vessel.

The method of the first embodiment wherein the bioreactor defines a volume of fermentation broth, the fermentation broth being passed to the vacuum distillation vessel at a feed rate, the feed rate being defined in terms of bioreactor volumes per hour, the feed rate being between 0.05 and 0.5.

The method of the first embodiment wherein the fermentation broth defines a residence time, the residence time being defined as an amount of time the fermentation broth is within the vacuum distillation vessel, the residence time being between 0.5 and 15 minutes.

The method of the first embodiment wherein the vacuum distillation vessel defines a separation section comprised of a series of distillation trays.

The method of the first embodiment wherein the vacuum distillation vessel defines a separation section comprised of more than three distillation stages.

The method of the first embodiment wherein the vacuum distillation vessel defines a separation section comprised of a packing material.

The method of the first embodiment wherein the product depleted stream comprises microbial biomass that is at least 20 percent viable.

The method of the first embodiment wherein the product depleted stream comprises less than 10% of the ethanol and isopropanol in the fermentation broth.

The method of the first embodiment wherein the vacuum distillation vessel defines a pressure drop over a height of the vacuum distillation vessel, the pressure drop being less than 3.2 kPa (absolute).

The method of the first embodiment wherein the vacuum distillation vessel is operated at a pressure between 4 kPa (absolute) and 10 kPa (absolute).

The method of the first embodiment wherein the vacuum distillation vessel is operated at a temperature between 30° C. and 50° C.

The method of the first embodiment wherein the product depleted stream is passed to a cooling means to reduce the temperature of the product depleted stream prior to the product depleted stream being passed to the bioreactor.

The method of the first embodiment wherein the temperature of the product depleted stream is between 30° C. and 40° C.

The method of the first embodiment further comprising degassing at least a portion of the fermentation broth prior to passing the fermentation broth to the vacuum distillation vessel.

The method of the first embodiment wherein the bioreactor is operated under conditions for fermentation of a C1-containing gas from an industrial process.

The method of the first embodiment wherein the industrial process is selected from the group comprising: carbohydrate fermentation, gas fermentation, cement making, pulp and paper making, steel making, oil refining and associated processes, petrochemical production, coke production, anaerobic or aerobic digestion, gasification, pyrolysis, torrefaction, natural gas extraction, oil extraction, metallurgical processes, and catalytic processes.

A second embodiment is a method for recovering product from a product enriched stream, the method comprising:
  a. passing a product enriched stream, comprising ethanol and isopropanol, to a dehydration reactor;
  b. dehydrating the product enriched stream to produce a dehydrated product stream comprising ethylene and propylene, and a water-rich stream; and
  c. passing the water-rich stream to the bioreactor.

The method of the second embodiment wherein at least a portion of the product enriched stream is received from a vacuum distillation vessel operated at conditions to partially vaporize a fermentation broth comprising microbial biomass, ethanol, and isopropanol, to produce the product enriched stream and a product depleted stream comprising microbial biomass.

The method of the second embodiment wherein at least a portion of the product enriched stream is received from a distillation vessel operated at conditions to distill a fermentation broth comprising ethanol, isopropanol, and water to produce a product enriched stream comprising ethanol and isopropanol and a product depleted stream comprising water.

The method of the second embodiment wherein the bioreactor is operated under conditions for fermentation of a C1-containing gas from an industrial process.

The method of the second embodiment wherein the dehydration reactor is operated at a temperature between 200° C. and 500° C.

The method of the second embodiment wherein the dehydration reactor is operated at a pressure from 0 MPa (gauge) to 8.3 MPa (gauge).

The method of the second embodiment wherein the product enriched stream is passed to the dehydration reactor at a weight hourly space velocity between 0.1 $h^{-1}$ to 30 $h^{-1}$.

The method of the second embodiment wherein the product enriched stream comprises 20 to 100 wt. % ethanol.

The method of the second embodiment wherein the dehydration reactor comprises at least one catalyst selected from the group consisting of alumina, modified alumina, crystalline or amorphous silicoaluminate, and modified silicoaluminate.

The method of the second embodiment wherein at least a portion of the dehydrated product stream is further converted to at least portion of a hydrocarbon fuel.

The method of the second embodiment, wherein at least a portion of the dehydrated product stream is polymerized.

The method of the second embodiment wherein at least a portion of the dehydrated product stream is separated into an ethylene-rich stream and a propylene-rich stream prior to being polymerized.

A third embodiment is a method for recovering product from a product enriched stream, the method comprising:
  a. passing a product enriched stream, comprising ethanol and isopropanol, to an extractive distillation vessel; and
  b. distilling the product enriched stream in the presence of an extractive distillation agent to obtain an overhead product and distillation bottoms, wherein
    i. at least a portion of the isopropanol is recovered in the overhead product and at least a portion of the ethanol is recovered in the distillation bottoms; or
    ii. at least a portion of the ethanol is recovered in the overhead product and at least a portion of the isopropanol is recovered in the distillation bottoms.

The method of the third embodiment wherein at least a portion of the product enriched stream is received from a distillation vessel operated at conditions to distill a fermentation broth comprising ethanol, isopropanol, and water to produce a product enriched stream comprising ethanol and isopropanol and a product depleted stream comprising water.

The invention claimed is:

1. A method for recovering product from a fermentation broth, the method comprising:
   a) passing a fermentation broth comprising microbial biomass, ethanol, and isopropanol from a bioreactor to a vacuum distillation vessel;
   b) partially vaporizing the fermentation broth to produce a product enriched stream, the product enriched stream comprising ethanol, and isopropanol, and a product depleted stream, the product depleted stream comprising microbial biomass;
   c) passing the product enriched stream to a rectification column to remove excess water and obtain a first overhead product stream;
   d) passing at least a portion of the product depleted stream back to the bioreactor;
   e) passing at least a portion of the first overhead product stream to an extractive distillation vessel; and f) distilling the first overhead product stream in the extractive distillation vessel in the presence of an extractive distillation agent to obtain a second overhead product stream and a distillation bottoms stream, wherein:
   i) at least a portion of the ethanol is recovered in the second overhead product stream and at least a portion of the isopropanol is recovered in the distillation bottoms stream; or
   ii) at least a portion of the isopropanol is recovered in the second overhead product stream and at least a portion of the ethanol is recovered in the distillation bottoms stream.

2. The method of claim 1, wherein at least a portion of the ethanol is recovered in the second overhead product stream and at least a portion of the isopropanol is recovered in the distillation bottoms stream; and wherein the extractive distillation agent comprises at least one material selected from the group consisting of alpha-pinene, beta-pinene, methyl isobutyl ketone, limonene, alpha-phellandrene, alpha-terpinene, myrcene, carane, p-mentha-1,5-diene, butyl ether, 1-methoxy-2-propanol, n-butyl acetate, n-amyl acetate, benzyl acetate, ethylene glycol ethyl ether acetate, methyl acetoacetate, ethylene glycol diacetate, 2-butoxyethyl acetate, methyl butyrate, ethyl propionate, ethyl n-valerate, butyl benzoate, ethyl benzoate, pyridine, N,N-dimethyl aniline, o-sec·butyl phenol, 3-isopropyl phenol, 2,6-dimethyl phenol, o-tert·butyl phenol, 4-ethyl phenol, diethyl phthalate, diisooctyl phthalate, dimethyl adipate, glycerine triacetate, diethyl malonate, dimethyl glutarate, tetrahydrofuran, ethylene glycol phenyl ether, dipropylene glycol methyl ether acetate, diethylene glycol hexyl ether, propoxypropanol, butoxypropanol, p-xylene glycol dimethyl ether, diethylene glycol t-butyl ether methyl ether, triethylene glycol diacetate, anisole, phenetole, phenyl ether, 1,2-methylenedioxybenzene, isophorone, ethyl-3-ethoxypropionate, tetraethylorthosilicate, 2-hydroxyacetophenone, 1,1,1-trichloroethane, tetrachloroethylene, 2,2,2-trichloroethanol, m-dichlorebenzene, chlorobenzene, 2,6-dichlorotoluene, 1-chlorohexane, diethylene glycol, dimethyl sulfoxide, dimethylformamide, sulfolane, isophorone, 2-pyrrolidione, 1-methyl-2pyrrolindinone, isodecyl alcohol, cyclododecanol, benzyl alcohol, 1-dodecanol, tridecyl alcohol, phenethyl alcohol, cyclohexanol, cyclopentanol, 2-nitropropane, 1-nitropropane, nitro-ethane, nitromethane, 3-nitrotoluene, 2-nitrotoluene, triacetin, 3-nitro-o-xylene, 1,4-dioxane, isobutyl acetate, ethyl butyrate, isoamyl formate, methyl caproate, ethyl caproate, propyl caproate, 1-methoxy-2-propanol acetate, isobutyl isobutyrate, hexyl acetate, ethyl isobutyrate, propyl butyrate, isobutyl butyrate, isobornyl acetate, 1,3-dioxolane, nitrobenzene, butyl butyrate, 4-methyl-2-pentanone, and polyethylene glycol 400.

3. The method of claim 1, wherein at least a portion of the isopropanol is recovered in the second overhead product stream and at least a portion of the ethanol is recovered in the distillation bottoms stream; and wherein the extractive distillation agent comprises at least one material selected from the group consisting of ethyl benzene, toluene, p-xylene, heptane, phenol, and 2-tert-butyl phenol.

4. The method of claim 1, wherein the extractive distillation agent is added to the extractive distillation vessel at least at a 5:1 extractive distillation agent to isopropanol ratio or at least a 5:1 extractive distillation agent to ethanol ratio.

5. The method of claim 1, wherein the fermentation broth further comprises one or more by-product selected from the group consisting of acetic acid, 3-hydroxybutyrate, isobutanol, n-propanol, n-butanol, and/or 2,3-butanediol.

6. The method of claim 5, wherein at least a portion of at least one by-product is removed through a side draw from the rectification column.

7. The method of claim 1, wherein the extractive distillation vessel is heat integrated.

8. The method of claim 1, further comprising:
passing the distillation bottoms stream to a separation vessel to produce an isopropanol-enriched stream or an ethanol-enriched stream; and an extractive distillation agent enriched stream; and passing at least a portion of the extractive distillation agent enriched stream to the extractive distillation vessel.

9. The method of claim 1, wherein the bioreactor defines a volume of fermentation broth, the fermentation broth being passed to the vacuum distillation vessel at a feed rate, the feed rate being defined in terms of bioreactor volumes per hour, the feed rate being between 0.05 and 0.5.

10. The method of claim 1, wherein the fermentation broth has a residence time within the vacuum distillation vessel between 0.5 and 15 minutes.

11. The method of claim 1, wherein the vacuum distillation vessel defines a separation section comprised of a series of distillation trays.

12. The method of claim 1, wherein the vacuum distillation vessel defines a separation section comprised of more than three distillation stages.

13. The method of claim 1, wherein the vacuum distillation vessel defines a separation section comprised of a packing material.

14. The method of claim 1, wherein the product depleted stream comprises microbial biomass that is at least 20 percent viable.

15. The method of claim 1, wherein the product depleted stream comprises less than 10% of the ethanol and isopropanol in the fermentation broth.

16. The method of claim 1, wherein the vacuum distillation vessel defines a pressure drop over a height of the vacuum distillation vessel, the pressure drop being less than 3.2 kPa (absolute).

17. The method of claim 1, wherein the vacuum distillation vessel is operated at a pressure between 4 kPa (absolute) and 10 kPa (absolute).

18. The method of claim 1, wherein the product depleted stream is passed to a cooling means to reduce the temperature of the product depleted stream prior to the product depleted stream being passed to the bioreactor.

19. The method of claim 18, wherein the temperature of the product depleted stream is between 30° C. and 40° C.

20. The method of claim 1, further comprising degassing at least a portion of the fermentation broth prior to passing the fermentation broth to the vacuum distillation vessel.

21. The method of claim 1, wherein the bioreactor is operated under conditions for fermentation of a C1-containing gas from an industrial process.

22. The method of claim 21, wherein the industrial process is selected from the group comprising: carbohydrate fermentation, gas fermentation, cement making, pulp and paper making, steel making, oil refining and associated processes, petrochemical production, coke production, anaerobic or aerobic digestion, gasification, pyrolysis, torrefaction, natural gas extraction, oil extraction, metallurgical processes, and catalytic processes.

23. The method of claim 2 wherein the extractive distillation agent is methyl isobutyl ketone.

24. The method of claim 1, wherein the first overhead product stream further comprises acetone and before passing the first overhead product stream to the extractive distillation vessel, the first overhead product stream is passed to a heat exchanger to produce an acetone containing stream which is recycled to the bioreactor.

25. The method of claim 1 where the first overhead product stream is first passed through a dehydration membrane system, to further remove excess water before, being passed to the extractive distillation vessel.

* * * * *